United States Patent [19]

Gould et al.

[11] 4,346,602

[45] Aug. 31, 1982

[54] APPARATUS AND METHOD FOR MEASURING ADHESIVE BOND STRENGTH

[75] Inventors: Larry D. Gould, West Canaan; Donald E. Garfield, Meriden, both of N.H.

[73] Assignee: The United States of America as represented by the Secretary of the Army, Washington, D.C.

[21] Appl. No.: 198,977

[22] Filed: Oct. 21, 1980

[51] Int. Cl.³ .................. G01N 3/24; G01N 33/44
[52] U.S. Cl. .................... 73/842; 73/150 A
[58] Field of Search ............... 73/150 A, 842

[56] References Cited

U.S. PATENT DOCUMENTS

T 916,005  11/1973  Dolen et al.
2,720,106  10/1955  Lippman
3,030,797   4/1962  Lacks et al.
3,046,567  10/1968  Terry

FOREIGN PATENT DOCUMENTS 197801  1/1975  U.S.S.R. .................... 73/150 A

Primary Examiner—S. Clement Swisher

Attorney, Agent, or Firm—Darrell E. Hollis

[57] ABSTRACT

An improved apparatus is disclosed for measuring the adhesive bond strength between two materials. A short, cylindrical specimen (28) having a test surface of one material is attached to a rigid base (12) on which a slide (16) is mounted on preloaded rollers (22) for movement along a pair of tracks (14) provided on the base. Above the specimen, a rigid mold block (36) is supported on an axially extending arm (24) formed integrally with the slide (16). The peripheries (32, 38) of the specimen and the mold block are essentially aligned so that seal ring (50) may be moved into engagement with a narrow gap formed between the specimen and the mold block. The second material, whose adhesive bond to the first material is to be determined, is introduced into the volume defined between the mold block and the specimen and caused or allowed to solidify there. The seal ring is then moved away from the gap and a force is applied to the slide to move it along the base, thereby applying a shear force to the adhesive bond between the two materials. The force and deformation are measured at which failure of the adhesive bond occurs. A method of using such an apparatus also is disclosed.

20 Claims, 2 Drawing Figures

APPARATUS AND METHOD FOR MEASURING ADHESIVE BOND STRENGTH

TECHNICAL FIELD

The invention relates to a method and apparatus for determining the adhesive bond strength of one material to another. Particularly, the invention concerns methods and apparatuses for measuring such bond strengths by applying shear force to a planar joint between the materials.

BACKGROUND ART

Numerous techniques have been developed through the years for measuring the adhesive bond strength of one material to another. In one type of test, a lap joint is formed from two substrates joined by a layer of adhesive material. Force is then applied to the substrates as close to parallel to the joint as possible, until failure occurs. This type of joint loading is thought to create a rather complex stress distribution since cleavage or peel may occur which may obscure adhesive shear properties. In another prior art test, a butt joint is formed and shear force is then applied to the adhesive joint. This type of test is reliable only if the test surfaces are very accurately aligned during testing; otherwise, unrestrained bending moments are introduced which affect the accuracy of the test.

Thus, a need has continued to exist for a simplified apparatus and method for measuring adhesive bond strength in which the stress applied to the test joint is limited essentially to shear stress, thus minimizing the effect of complex stress distributions on the desired measurement of adhesive shear strength.

DISCLOSURE OF THE INVENTION

A primary object of the present invention is to provide simple, reliable apparatus and method for measuring adhesive bond strength in which complex cleavage stresses caused by unrestrained bending of the sample specimen are minimized during actual testing.

A further object of the invention is to provide such an apparatus in which the rugged design of the apparatus ensures proper maintenance of dimensional relationships both during formation of the test sample and application of force to the sample during actual testing, thereby ensuring uniform test results.

Another object of the invention is to provide an improved fixture for making test samples, the fixture being adaptable for use in conventional tension and compression testing machines.

Still another object of the invention is to provide such an apparatus which is suitable for use with a variety of adhesive-material couples.

These objectives are given only by way of example; thus, other desirable objectives inherently achieved by the disclosed apparatus and method may occur or become apparent to those skilled in the art. Nonetheless, the scope of the invention is to be limited only by the appended claims.

The method according to the invention is of general utility. A specimen of a first material is provided, having a preferably flat test surface. A rigid mold block having a further surface is positioned opposite the specimen to define a narrow gap between their surfaces, the gap having a perimeter. A seal is applied across this gap at the perimeter to define a mold volume between the specimen, block and seal into which a second, liquid material is introduced. The second material is caused or permitted to solidify, such as by freezing, fusing, curing, crystallizing and so forth after which the seal is removed. Then, by moving the mold block and specimen relative to each other in a direction transverse to the test surface, the force and deformation at which the adhesive bond fails may be determined.

In the apparatus according to the invention, a rigid base is provided on which a specimen of a first material is fixed. The specimen includes an upwardly facing, preferably flat test surface which cooperates with a means for providing a layer of a second material adhesively bonded to the test surface. Further means are provided for mounting the first means for relative movement transverse to the test surface. Means such as an hydraulic ram is used to apply force to the second means and means such as a load cell is used to determine the magnitude of the force at which the adhesive bond fails between the two materials.

In the preferred embodiment of the invention, the test surface is situated opposite a rigid block, the test surface and the block preferably having essentially congruent, cylindrical perimeters. The block and test surface are spaced a small, uniform distance from each other and an elastic seal ring is used to close the gap defined between them at their perimeters. Means such as a downwardly extending bore are provided for introducing a second material in a liquid state into the volume defined beteeen the test surface and the block, where the second material is permitted or caused to solidify. The portion of the second material which solidifies above the test surface within the mold block also acts as a key or handle for transmitting force to the test surface.

Preferably, both the specimen and the rigid block are provided with exterior walls extending away from the test surface at or near its perimeter so that the previously mentioned seal ring may comprise an elastic ring which seals against these exterior walls on either side of the gap between the test surface and the rigid block.

BEST MODE FOR CARRYING OUT THE INVENTION

Figure 1:
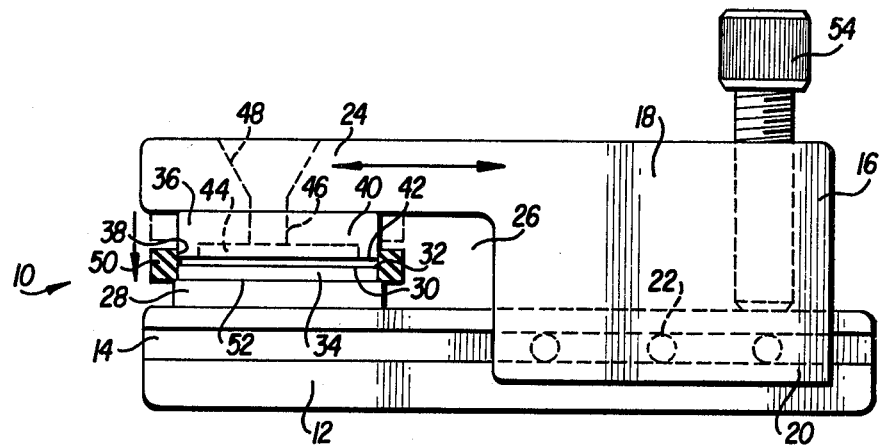
FIG. 1 shows a side elevation view, partially in section and partially in phantom, of a fixture according to the present invention which is particularly suited for forming a test sample for determining adhesive bond strength.

The following is a detailed description of the preferred embodiments of the invention, reference being made to the drawing in which like reference numerals identify like elements of structure in the two Figures.

FIG. 1 illustrates a fixture for preparing a test sample particularly suited for use in accordance with the present invention. The fixture 10 comprises a rigid rectangular base 12 which may be made from steel or similar material. The opposite vertical sides of base 12 are provided with parallel horizontal guide tracks or grooves 14, only one of which is visible in FIG. 1. Mounted for horizontal movement on tracks 14 is a slide 16 which also may be made from steel and comprises a rigid body portion 18 having a pair of spaced, rigid downwardly extending roller support flanges 20, only one of which is visible in FIG. 1. Each of support flanges 20 is provided on its inner surface with a plurality of rollers or roller bearings 22, shown in phantom, which ride in tracks 14. Rollers 22 are preloaded or tightly fitted in track 14 so as to effectively limit the movement of slide 16 to horizontal traverses above base 12. A rigid axially extending support arm 24 is formed integrally with and extends from body portion 18 parallel to and at a distance 26 from the upper surface of base 12.

Secured to the upper surface of base 12 by any suitable means is a single material specimen 28, preferably cylindrical in geometry, having a flat upper test surface 30 with a periphery 32. A coating of other test material may be provided on surface 30, such as an antiicing coating if ice adhesion is to be tested. Extending downwardly from periphery 32 is an essentially cylindrical wall 34. Opposite specimen 28 and attached to the underside of support arm 24 is a rigid mold block 36, also preferably cylindrical in configuration. Extending upwardly from the periphery 38 of mold block 36 is a wall 40 which preferably is aligned with wall 34 so that their peripheries are congruent. A radially extending flat peripheral lip 42 is provided on the under surface of mold block 36 surrounding an interior, concave mold cavity 44, shown in phantom. The bottom surface of lip 42 should be equally spaced from test surface 30 around its periphery so that a uniform gap will exist between mold block 36 and test surface 30. Typically, a gap on the order of a few ten-thousandths of an inch is sufficient, though different materials may require the use of different gaps for optimum results. An upwardly opening bore 46 (in phantom) is provided at the top of mold cavity 44 and connects to a funnel-shaped bore 48 (in phantom) provided through the thickness of support arm 24.

The gap between mold block 36 and specimen 28 may be closed by an elastomeric seal ring 50 which is snuggly fitted around wall 40 of mold block 36. Seal ring 50 may be moved up wall 40 to a position abutting the underside of support arm 24, as shown in phantom, during actual testing; or, it may be moved to the position illustrated in FIG. 1 in which it seals against both walls 34 and 40 and rests against a stop ledge 52 which may be provided on specimen 28.

To prepare a sample for testing, seal ring 50 is moved to its illustrated position and slide 16 is locked in position by tightening a lock bolt 54 which is threaded through slide 16 into contact with base 12. The material whose adhesive bond to specimen 28 is to be determined is then introduced in liquid form into cavity 44 through bores 46 and 48. The material is then caused or permitted to solidify within cavity 48, after which the seal ring 50 is moved to its upper position and lock bolt 54 is loosened. For example, if ice is the material whose bond is to be determined, the entire fixture shown in FIG. 1 is cooled to below 0° C. and water is poured into the mold cavity and caused to freeze there. Of course, various liquid adhesives may be used.

Figure 2:
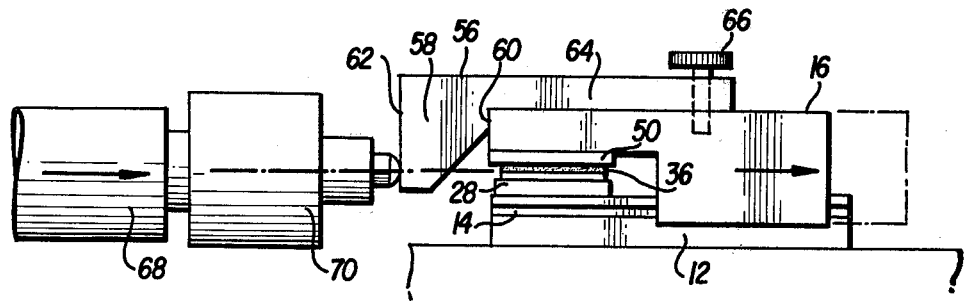
FIG. 2 shows a side elevation view of an apparatus for determining adhesive bond strength in which the fixture of FIG. 1 is incorporated.

The sample thus prepared is then incorporated in the apparatus illustrated in FIG. 2. Base plate 12 is clamped to the bed of an appropriate test stand and a loading adapter 56 is attached to fixture 10 as illustrated. The adapter includes a head portion 58 having a surface 60 which abuts one end of support arm 24 and a parallel surface 62 against which force is applied during testing. A rigid axially extending attachment arm 64 formed integrally with head portion 58 rests on and is attached to the upper surface of support arm 24 by means such as a set screw 66. An hydraulic ram 68 acting in the same plane with surface 30 and including a load cell 70 is then brought into contact with surface 62 at a constant velocity and the force and deformation at which the adhesive bond fails are determined. During application of the load, the solidified portion of the second material extending into volume 44 acts as a key or handle to transmit force to the adhesive joint at surface 30. Failure occurs at surface 30 within the first ten or fifteen thousandths of an inch of movement of slide 16. In this range, the preload of rollers 22 ensures that an essentially pure shear load is applied to the adhesive joint.

INDUSTRIAL APPLICABILITY

The apparatus and method according to the present invention are particularly well-suited for determining the adhesive bond strength of ice to an underlying substrate, such as a specimen of the exterior wall of an air craft component; however, other adhesives also may be tested.

Having described our invention in sufficient detail to enable those skilled in the art to make and use it, we claim:

1. Apparatus for determining the adhesive bond strength of one material to another, comprising:
    (a) a rigid base;
    (b) a specimen of a first material fixed to said base and provided with a test surface;
    (c) first means for providing a layer of a second material bonded to said test surface;
    (d) means for selectively providing a fluid-tight seal between said test surface and said first means;
    (e) second means for mounting said first means for movement relative to said test surface;
    (f) third means for applying a force to cause relative movement between said base and said first means whereby the joint between said layer and said specimen is stressed; and
    (g) fourth means for determining the magnitude of said force at which the adhesive bond fails between said first and second materials.

2. Apparatus according to claim 1, wherein said test surface has a first perimeter; and said first means comprises a rigid block having a second perimeter and a further surface facing said test surface, said sealing means sealing the gap defined between said surfaces at said perimeters, and means for introducing said second material in a liquid state into the volume defined between said surfaces, for solidification to form said layer.

3. Apparatus according to claim 2, wherein said perimeters are substantially identical and said sealing means comprises an elastic ring which closes said gap.

4. Apparatus according to claim 2, wherein said specimen has a first exterior wall extending away from said test surface at said first perimeter and said rigid block has a second exterior wall extending away from said further surface at said second perimeter, said sealing means comprising an elastic ring which seals against said exterior walls on either side of said gap.

5. Apparatus according to claim 4, wherein said elastic ring is adapted to be moved along said first exterior wall surface away from said gap following solidification of said second material.

6. Apparatus according to claim 2, further comprising means for selectively locking said rigid block to prevent its movement relative to said test surface until said layer has solidified.

7. Apparatus according to claim 2, wherein said further surface is at least partially concave within said further perimeter.

8. Apparatus according to claim 2, wherein said introducing means comprises an upwardly opening bore in said rigid block through which said second material flows into said volume.

9. Apparatus according to claim 1, wherein said second means comprises at least one track in said base parallel to said test surface, a support for said first means and roller means positioned between said support and said track for facilitating said movement.

10. Apparatus according to claim 2, wherein said applying means directs its force along an axis passing through the center of said gap.

11. A method for determining the adhesive bond strength of one material to another, comprising the steps of:
providing a specimen of a first material, said specimen having a test surface;
providing a block having a further surface;
positioning said block opposite said specimen to define a gap between said surfaces, said gap having a perimeter;
applying a seal across said gap at said perimeter to define a volume between said specimen, block and seal;
introducing a second liquid material into said volume;
causing said second material to solidify;
removing said seal;
moving said block and specimen relative to each other in a direction transverse to said test surface; and
measuring the force at which the adhesive bond fails between said first and second materials.

12. Apparatus for preparing a test sample for measuring the adhesive bond strength of one material to another, comprising:
(a) a rigid base;
(b) a specimen of a first material fixed to said base and provided with a test surface;
(c) first means for providing a layer of a second material bonded to said test surface;
(d) means for selectively providing a fluid-tight seal between said test surface and said first means; and
(e) second means for mounting said first means for movement relative to said test surface, whereby the adhesive bond between said first and second materials is stressed.

13. Apparatus according to claim 12, wherein said test surface has a first perimeter; and said first means comprises a rigid block having a second perimeter and a further surface facing said test surface, said sealing means sealing the gap defined between said surfaces at said perimeters, and means for introducing said second material in a liquid state into the volume defined between said surfaces, for solidification to form said layer.

14. Apparatus according to claim 13, wherein said perimeters are substantially identical and said sealing means comprises an elastic ring which closes said gap.

15. Apparatus according to claim 13, wherein said specimen has a first exterior wall extending away from said test surface at said first perimeter and said rigid block has a second exterior wall extending away from said further surface at said second perimeter, said sealing means comprising an elastic ring which seals against said exterior walls on either side of said gap.

16. Apparatus according to claim 15, wherein said elastic ring is adapted to be moved along said first exterior wall surface away from said gap following solidification of said second material.

17. Apparatus according to claim 13, further comprising means for selectively locking said rigid block to prevent its movement relative to said test surface until said layer has solidified.

18. Apparatus according to claim 13, wherein said further surface is at least partially concave within said further perimeter.

19. Apparatus according to claim 13, wherein said introducing means comprises an upwardly opening bore in said rigid block through which said second material flows into said volume.

20. Apparatus according to claim 12, wherein said second means comprises at least one track in said base parallel to said test surface, a support for said first means and roller means positioned between said support and said track for facilitating said movement.

* * * * *